United States Patent
Stoyka, Jr.

[11] Patent Number: 6,068,475
[45] Date of Patent: May 30, 2000

[54] FLAVORED AND MEDICATED THERAPEUTIC MOUTHPIECE

[76] Inventor: Frank S. Stoyka, Jr., 1461 Sheridan Dr., Parma, Ohio 44134

[21] Appl. No.: 09/248,714

[22] Filed: Feb. 11, 1999

[51] Int. Cl.⁷ .................................................. A61G 17/02
[52] U.S. Cl. ................................ 433/80; 433/37; 128/861
[58] Field of Search ..................... 433/80, 6, 37, 433/48, 216, 215; 128/863, 859, 861

[56] References Cited

U.S. PATENT DOCUMENTS

| | | |
|---|---|---|
| D. 246,671 | 12/1977 | Cerniway . |
| 803,475 | 10/1905 | Dennis ........................................ 433/80 |
| 3,096,761 | 7/1963 | Moffett . |
| 3,532,091 | 10/1970 | Lerman . |
| 3,624,909 | 12/1971 | Greenberg ................................. 433/80 |
| 3,964,489 | 6/1976 | Kesselring . |
| 4,064,628 | 12/1977 | Weitzman ................................. 128/260 |
| 4,138,814 | 2/1979 | Weitzman . |
| 4,240,436 | 12/1980 | Singleton . |
| 4,983,122 | 1/1991 | Mitnick . |
| 5,211,559 | 5/1993 | Hart et al. ................................. 433/80 |
| 5,323,787 | 6/1994 | Pratt . |
| 5,509,801 | 4/1996 | Nicholson ................................. 433/80 |
| 5,620,011 | 4/1997 | Flowers . |
| 5,819,744 | 10/1998 | Stoyka, Jr. ................................. 128/859 |
| 5,924,863 | 7/1999 | Jacobs et al. .............................. 433/80 |

Primary Examiner—Gene Mancene
Assistant Examiner—Pedro Philogene

[57] ABSTRACT

A flavored and medicated therapeutic mouthpiece for causing a mouth to salivate and for dispensing medicine to heal wounds and sores within the mouth. The flavored and medicated therapeutic mouthpiece includes a pliable U-shaped member insertable into a mouth of a user. A first flavored coating is disposed on the U-shaped member. A second flavored coating or a layer of medicine may also be applied to the U-shaped member. The U-shaped member may be hollow and have a cold temperature storage medium stored therein.

19 Claims, 2 Drawing Sheets

FLAVORED AND MEDICATED THERAPEUTIC MOUTHPIECE

BACKGROUND OF THE INVENTION

1. Field of the Invention

The present invention relates to medicated oral devices and more particularly pertains to a new flavored and medicated therapeutic mouthpiece for causing a mouth to salivate and for dispensing medicine to heal wounds and sores within the mouth.

2. Description of the Prior Art

The use of medicated oral devices is known in the prior art. More specifically, medicated oral devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,819,744; U.S. Pat. No. 4,983,122; U.S. Pat. No. 5,323,787; U.S. Pat. No. 4,138,814; U.S. Pat. No. 3,964,489; U.S. Pat. No. Des. 246,671; and U.S. Pat. No. 4,240,436.

While these devices fulfill their respective, particular objectives and requirements, the aforementioned patents do not disclose a new flavored and medicated therapeutic mouthpiece. The inventive device includes a pliable U-shaped member insertable into a mouth of a user. A first flavored coating is disposed on the U-shaped member. A second flavored coating or a layer of medicine may also be applied to the U-shaped member. The U-shaped member may be hollow and have a cold temperature storage medium stored therein.

In these respects, the flavored and medicated therapeutic mouthpiece according to the present invention substantially departs from the conventional concepts and designs of the prior art, and in so doing provides an apparatus primarily developed for the purpose of for causing a mouth to salivate and for dispensing medicine to heal wounds and sores within the mouth.

SUMMARY OF THE INVENTION

In view of the foregoing disadvantages inherent in the known types of medicated oral devices now present in the prior art, the present invention provides a new flavored and medicated therapeutic mouthpiece construction wherein the same can be utilized for causing a mouth to salivate and for dispensing medicine to heal wounds and sores within the mouth.

The general purpose of the present invention, which will be described subsequently in greater detail, is to provide a new flavored and medicated therapeutic mouthpiece apparatus and method which has many of the advantages of the medicated oral devices mentioned heretofore and many novel features that result in a new flavored and medicated therapeutic mouthpiece which is not anticipated, rendered obvious, suggested, or even implied by any of the prior art medicated oral devices, either alone or in any combination thereof.

To attain this, the present invention generally comprises a pliable U-shaped member insertable into a mouth of a user. A first flavored coating is disposed on the U-shaped member. A second flavored coating or a layer of medicine may also be applied to the U-shaped member. The U-shaped member may be hollow and have a cold temperature storage medium stored therein.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new flavored and medicated therapeutic mouthpiece apparatus and method which has many of the advantages of the medicated oral devices mentioned heretofore and many novel features that result in a new flavored and medicated therapeutic mouthpiece which is not anticipated, rendered obvious, suggested, or even implied by any of the prior art medicated oral devices, either alone or in any combination thereof.

It is another object of the present invention to provide a new flavored and medicated therapeutic mouthpiece which may be easily and efficiently manufactured and marketed.

It is a further object of the present invention to provide a new flavored and medicated therapeutic mouthpiece which is of a durable and reliable construction.

An even further object of the present invention is to provide a new flavored and medicated therapeutic mouthpiece which is susceptible of a low cost of manufacture with regard to both materials and labor, and which accordingly is then susceptible of low prices of sale to the consuming public, thereby making such flavored and medicated therapeutic mouthpiece economically available to the buying public.

Still yet another object of the present invention is to provide a new flavored and medicated therapeutic mouthpiece which provides in the apparatuses and methods of the prior art some of the advantages thereof, while simultaneously overcoming some of the disadvantages normally associated therewith.

Still another object of the present invention is to provide a new flavored and medicated therapeutic mouthpiece for causing a mouth to salivate and for dispensing medicine to heal wounds and sores within the mouth.

Yet another object of the present invention is to provide a new flavored and medicated therapeutic mouthpiece which includes a pliable U-shaped member insertable into a mouth of a user. A first flavored coating is disposed on the U-shaped member. A second flavored coating or a layer of medicine may also be applied to the U-shaped member. The U-shaped member may be hollow and have a cold temperature storage medium stored therein.

Still yet another object of the present invention is to provide a new flavored and medicated therapeutic mouthpiece that may have a cold temperature storage medium disposed in a hollow interior thereof for reducing swelling and alleviating pain.

Even still another object of the present invention is to provide a new flavored and medicated therapeutic mouthpiece that may be made in several different colors.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
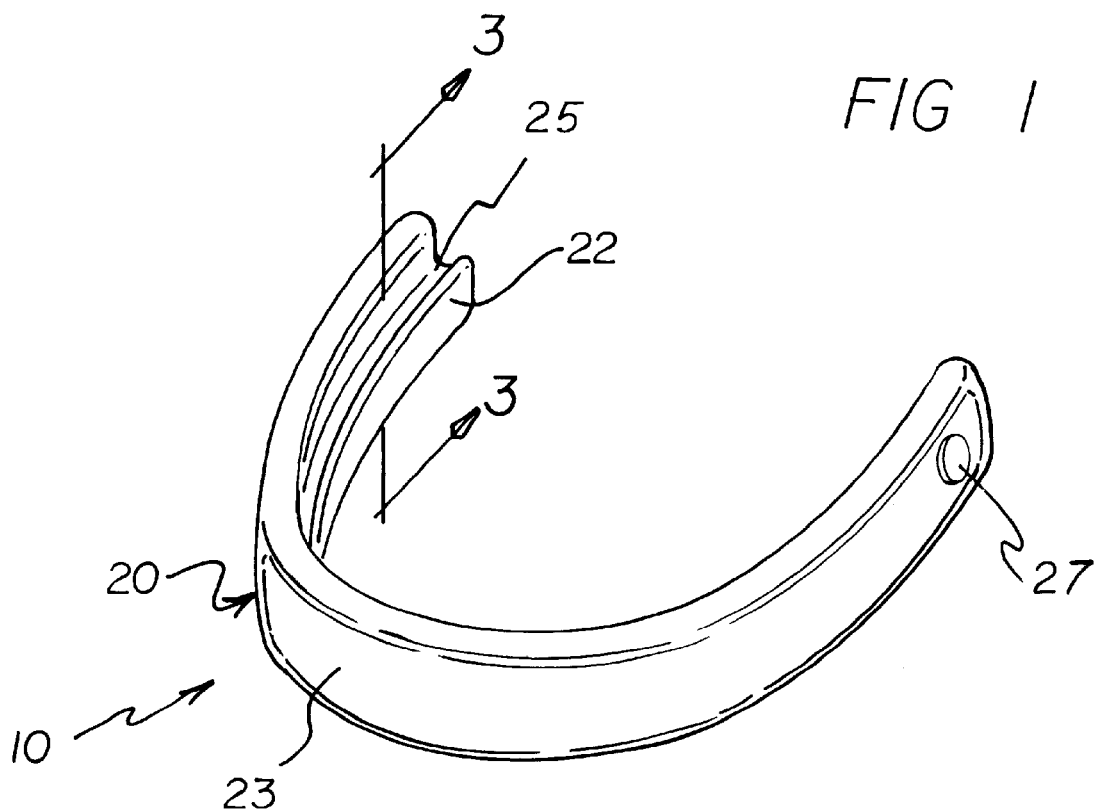
FIG. 1 is a schematic perspective view of a new flavored and medicated therapeutic mouthpiece according to the present invention.
Figure 3:
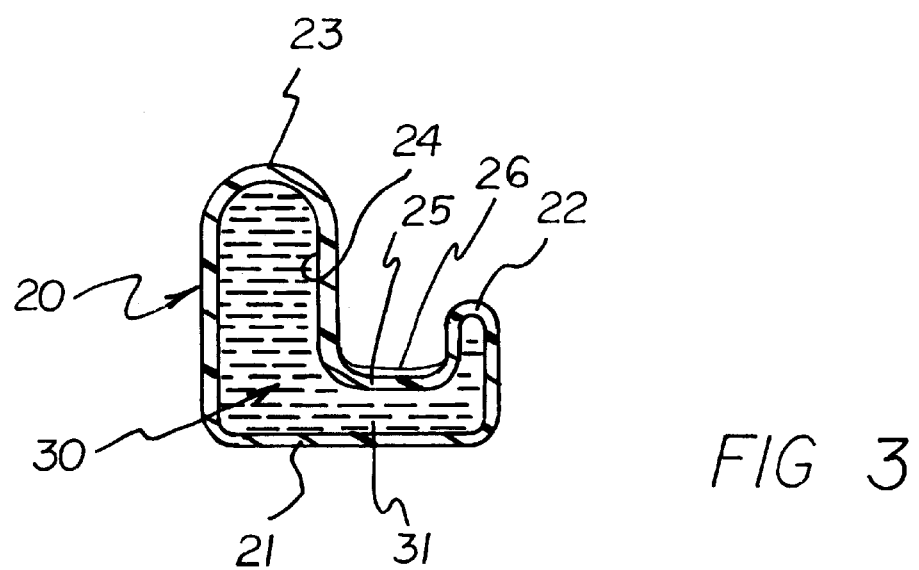
FIG. 3 is a schematic cross-sectional view of the present invention taken from line 3—3 of FIG. 1.
Figure 2:
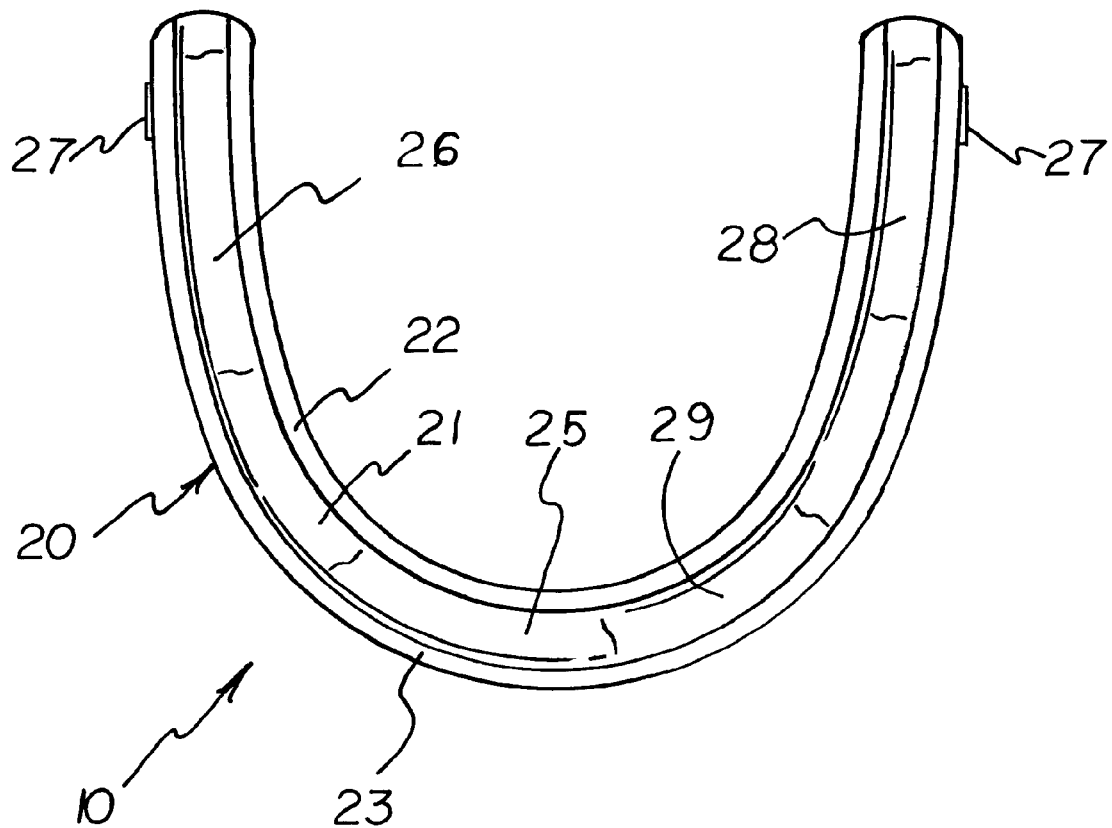
FIG. 2 is a schematic side view of the present invention.

With reference now to the drawings, and in particular to FIGS. 1 through 3 thereof, a new flavored and medicated therapeutic mouthpiece embodying the principles and concepts of the present invention and generally designated by the reference numeral 10 will be described.

As best illustrated in FIGS. 1 through 3, the flavored and medicated therapeutic mouthpiece 10 generally comprises a pliable U-shaped member 20 insertable into a mouth of a user. A first flavored coating 26 is disposed on the U-shaped member 20. A second flavored coating 28 or a layer of medicine 29 may also be applied to the U-shaped member 20. The U-shaped member 20 may be hollow and have a cold temperature storage medium 30 stored therein.

In more detail, it is seen that the U-shaped member 20 has a generally J-shaped cross-section. The U-shaped member 20 has a bottom wall portion 21, an integrally joined inner wall portion 22 perpendicularly extending from the bottom wall portion 21 along an inner periphery thereof, and an integrally joined outer wall portion 23 perpendicularly extending from the bottom wall portion 21 along an outer periphery thereof. Preferably, the outer wall portion 23 has a height greater than that of the inner wall portion 22. A tooth receiving channel 25 is formed between the inner and outer wall portion 23s.

Preferably, the U-shaped member 20 generally conforms in use to at least one of the upper teeth and the lower teeth of the mouth of the user. In particular, the bottom wall portion 21 abuts the occlusal surfaces of the teeth, the inner wall portion 22 abuts the lingual surfaces of the teeth, and the outer wall portion 23 abuts the buccal surfaces of the teeth and the adjacent gingival surface of the mouth when the U-shaped member 20 is positioned within the mouth of the user.

The first flavored coating 26 may be disposed in one portion of the tooth receiving channel 25 or anywhere on the U-shaped member 20. Preferably, the first flavored coating 26 has a sour or tart taste for causing the mouth to salivate, which may be desirable if applying medicine to the mouth that uses saliva as a transportation medium to disperse it throughout the mouth. The saliva also moistens the mouth naturally.

Alternatively or in combination with the first flavored coating 26, a second flavored coating 28 may be disposed in another portion of the tooth receiving channel 25 or anywhere on the U-shaped member 20.

Preferably, the second flavored coating 28 has a sweet taste so that using the mouthpiece is more bearable to small children and others who dislike using it. Children will be less likely to object to placing the mouthpiece in their mouths if the mouthpiece tastes like candy. The sweet taste could also counteract the sour tasting first flavored coating 26.

Alternatively or in combination with the flavored coatings, a quantity of first medicine 29 such as a salve, liquid, powder, or the like may be disposed in another portion of the tooth receiving channel 25 or anywhere on the U-shaped member 20. Placement in the tooth receiving channel 25 is desirable if a slower, controlled application of the medicine is desired. The first medicine 29 will be transported out of the channel slower before reaching skin where it may be absorbed or swallowed. Placement on the inner or outer wall portions 23 are desirable if the medicine is applied to a sore on the gumline or cheek. The medicine is simply applied to the mouthpiece at a position that will touch or be close to the sore spot.

Preferably, the U-shaped member 20 has a substantially hollow interior 24. The wall portions of the U-shaped member 20 is porous at a molecular level, much like a molecular sieve, such that only molecules smaller than a predetermined size are permitted to pass through the pores of the U-shaped member 20. A quantity of second medicine 31 is disposed substantially throughout the hollow interior 24 of the U-shaped member 20. The pores of the U-shaped member 20 permit passage of the second medicine 31 therethrough.

Ideally, the U-shaped member 20 has a pair of side openings 27 into the hollow interior 24 thereof adapted for permitting insertion or injection of the second medicine therethrough into the hollow interior 24 of the U-shaped member 20. The side openings 27 should be positioned towards free ends of the U-shaped member 20, as shown in FIG. 1, to provide the least discomfort. Once the second medicine 31 is inserted into the hollow interior 24, the U-shaped member 20 is squeezed along its length to disperse the second medicine 31 throughout the U-shaped member 20.

Optionally, a non-toxic cold temperature storage medium 30 may be disposed substantially throughout the hollow interior 24 of the U-shaped member 20. The cold temperature storage medium 30 would be disposed throughout the bottom wall portion 21, the inner wall portion 22, and the outer wall portion 23 of the U-shaped member 20.

Preferably, the cold temperature storage medium 30 comprises a gel-like compound characterized by an ability to remain cold for an extended period of time in ambient conditions. An exemplary gel-like compound is TEK-GEL™ marketed by ZERO-PAK PRODUCTS LTD., ZEROPAK@aol.com, Tel: (604) 278-4828, Fax: (604) 278-2636. Alternatively, the cold temperature storage medium 30 comprises a chemical mixture that becomes cold when agitated, useful in emergency kits.

When the cold temperature storage medium 30 is used in conjunction with the second medicine, the cold temperature storage medium 30 has a molecular size greater than the pores of the U-shaped member 20 so that it is trapped inside the U-shaped member 20, while the second medicine 31 is free to escape.

When the cold temperature storage medium 30 is used in conjunction with the sour tasting coating, a sensation of sucking water off of ice is created. Saliva is cooled by the cold temperature storage medium 30, creating the sensation. This would help people who suffer dry mouth caused by medicine, participation in sports, and at the work place.

The cold temperature storage medium 30 in the mouthpiece would give cooling relief to a baby with teething pain.

A second U-shaped member (not shown) may be provided, substantially as set forth in the preceding paragraphs, with a unique color different than a color of the U-shaped member. Ideally, several U-shaped members are produced in a variety of unique colors. This permits a child to choose his or her preferred color, which may make the child more willing to use the mouthpiece.

The mouthpieces may be made of glow in the dark material as well. This could help the user be seen at night, such as when jogging.

In use, the flavored coating or coatings 26,28 and/or first medicine 29 is applied to the outer surface of the U-shaped member 20 in the desired location. The second medicine 31 may be inserted in the hollow interior of the U-shaped member 20 and spread throughout by squeezing the U-shaped member 20 at various intervals along its length. If a cold mouthpiece is desired, it is placed in a cold area, such as in a refrigerator, to cool down the cold temperature storage medium 30. The user has the option of using a mouthpiece with no flavoring or medicine, with one or more flavorings and no medicine, medicine with no flavorings, or with flavorings and medicine. Any of these may or may not include the cold medium.

The U-shaped member 20 is positioned within the mouth of the user so as to fit over either the upper teeth or the lower teeth of the mouth. As such, the bottom wall portion 21 abuts the occlusal surfaces of the teeth, the inner wall portion 22 abuts the lingual surfaces of the teeth, and the outer wall portion 23 abuts the buccal surfaces of the teeth and the adjacent gingival surface of the mouth. When the U-shaped member 20 is positioned within the mouth of the user, the cold temperature storage medium 30 is optimally positioned so as to alleviate pain and reduce swelling within the mouth.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A mouthpiece, comprising:
    a pliable U-shaped member insertable into a mouth of a user;
    a first flavored coating being disposed on said U-shaped member; and
    wherein said U-shaped-member has a substantially hollow interior, said wall portions of said U-shaped member being porous such that only molecules smaller than a predetermined size are permitted to pass through pores of said U-shaped member, a quantity of second medicine being disposed substantially throughout said hollow interior of said U-shaped member, said pores of said U-shaped member permitting passage of said second medicine therethrough.

2. The mouthpiece of claim 1, wherein said U-shaped member having a generally J-shaped cross-section, said U-shaped member including a bottom wall portion, an integrally joined inner wall portion perpendicularly extending from said bottom wall portion along an inner periphery thereof, and an integrally joined outer wall portion perpendicularly extending from said bottom wall portion along an outer periphery thereof.

3. The mouthpiece of claim 1, wherein said U-shaped member has a tooth receiving channel.

4. The mouthpiece of claim 3, wherein said first flavored coating is disposed in one portion of said tooth receiving channel.

5. The mouthpiece of claim 1, wherein said first flavored coating has a sour taste for causing the mouth to salivate.

6. The mouthpiece of claim 1, further comprising a second flavored coating being disposed on said U-shaped member.

7. The mouthpiece of claim 6, wherein said second flavored coating having a sweet taste.

8. The mouthpiece of claim 1, further comprising a quantity of first medicine being disposed on said U-shaped member.

9. The mouthpiece of claim 1, wherein said U-shaped member has a pair of side openings into said hollow interior thereof adapted for permitting insertion of said second medicine therethrough.

10. The mouthpiece of claim 1, wherein said U-shaped member has a substantially hollow interior, a non-toxic cold temperature storage medium being disposed substantially throughout said hollow interior of said U-shaped member.

11. The mouthpiece of claim 10, wherein said cold temperature storage medium comprises a gel-like compound characterized by an ability to remain cold for an extended period of time in ambient conditions.

12. The mouthpiece of claim 10, wherein said cold temperature storage medium becomes cold when agitated.

13. The mouthpiece of claim 1, further comprising a non-toxic cold temperature storage medium being disposed substantially throughout said hollow interior of said U-shaped member, said cold temperature storage medium having a molecular size greater than said pores of said U-shaped member.

14. The mouthpiece of claim 1, wherein said U-shaped member has a substantially hollow interior, a non-toxic cold temperature storage medium being disposed substantially throughout said hollow interior of said U-shaped member.

15. The mouthpiece of claim 14, wherein said cold temperature storage medium comprises a gel-like compound characterized by an ability to remain cold for an extended period of time in ambient conditions.

16. The mouthpiece of claim 14, wherein said cold temperature storage medium becomes cold when agitated.

17. The mouthpiece of claim 14, further comprising a non-toxic cold temperature storage medium being disposed substantially throughout said hollow interior of said U-shaped member, said cold temperature storage medium having a molecular size greater than said pores of said U-shaped member.

18. A mouthpiece, comprising:

a pliable U-shaped member insertable into a mouth of a user, said U-shaped member having a generally J-shaped cross-section;

said U-shaped member including a bottom wall portion, an integrally joined inner wall portion perpendicularly extending from said bottom wall portion along an inner periphery thereof, and an integrally joined outer wall portion perpendicularly extending from said bottom wall portion along an outer periphery thereof;

said outer wall portion having a height greater than that of said inner wall portion;

said U-shaped member having a tooth receiving channel formed between said inner and outer wall portions;

said U-shaped member generally conforming in use to at least one of the upper teeth and the lower teeth of the mouth of the user whereby said bottom wall portion abuts the occlusal surfaces of the teeth, said inner wall portion abuts the lingual surfaces of the teeth, and said outer wall portion abuts the buccal surfaces of the teeth and the adjacent gingival surface of the mouth when said U-shaped member is positioned within the mouth of the user;

a first flavored coating being disposed in one portion of said tooth receiving channel;

said first flavored coating having a sour taste for causing the mouth to salivate;

a second flavored coating being disposed in another portion of said tooth receiving channel;

said second flavored coating having a sweet taste;

a quantity of first medicine being disposed in another portion of said tooth receiving channel;

said U-shaped member having a substantially hollow interior;

said wall portions of said U-shaped member being porous such that only molecules smaller than a predetermined size are permitted to pass through pores of said U-shaped member;

a quantity of second medicine being disposed substantially throughout said hollow interior of said U-shaped member, said pores of said U-shaped member permitting passage of said second medicine therethrough;

said U-shaped member having a pair of side openings into said hollow interior thereof adapted for permitting insertion of said second medicine therethrough;

a non-toxic cold temperature storage medium disposed substantially throughout said hollow interior of said U-shaped member;

said cold temperature storage medium comprising a gel-like compound characterized by an ability to remain cold for an extended period of time in ambient conditions;

wherein said gel-like compound becomes cold when agitated;

said cold temperature storage medium having a molecular size greater than said pores of said U-shaped member; and a second U-shaped member having a unique color different than a color of said U-shaped member.

19. A mouthpiece, comprising:

a pliable U-shaped member insertable into a mouth of a user;

a first flavored coating being disposed on said U-shaped member; and wherein said U-shaped member has a substantially hollow interior, a non-toxic cold temperature storage medium being disposed substantially throughout said hollow interior of said U-shaped member.

* * * * *